United States Patent [19]

Smith

[11] 4,206,311

[45] Jun. 3, 1980

[54] 2-DECARBOXY-2-HYDROXY-METHYL-13,14-DIDEHYDRO-17-PHENYL PGF COMPOUNDS

[75] Inventor: Herman W. Smith, Kalamazoo, Mich.

[73] Assignee: The Upjohn Company, Kalamazoo, Mich.

[21] Appl. No.: 880,740

[22] Filed: Feb. 24, 1978

Related U.S. Application Data

[62] Division of Ser. No. 814,410, Jul. 11, 1977, Pat. No. 4,137,270, which is a division of Ser. No. 708,752, Jul. 26, 1976, Pat. No. 4,058,564.

[51] Int. Cl.$^2$ ............................................. C07C 35/21
[52] U.S. Cl. .................................. 568/660; 568/646; 568/807
[58] Field of Search ..................... 568/807, 646, 660

[56] References Cited

U.S. PATENT DOCUMENTS 3,932,496  1/1976  Jung ..................................... 260/514

*Primary Examiner*—Robert Gerstl
*Attorney, Agent, or Firm*—Robert A. Armitage

[57] ABSTRACT

This invention comprises certain analogs of the prostaglandins in which the C-1 carboxyl is replaced by a primary alcohol and the double bond between C-13 and C-14 is replaced by a triple bond. Also provided in this invention, are novel chemical processes useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

71 Claims, No Drawings

2-DECARBOXY-2-HYDROXY-METHYL-13,14-DIDEHYDRO-17-PHENYL PGF COMPOUNDS

The present application is a divisional application of Ser. No. 814,410, filed July 11, 1977, now U.S. Pat. No. 4,137,270, which application is a divisional application of Ser. No. 708,752, filed July 26, 1976, issued as U.S. Pat. No. 4,058,564 on Nov. 15, 1977.

The present invention relates to prostaglandin analogs for which the essential material constituting a disclosure therefor is incorporated by reference here from U.S. Pat. No. 4,058,564, issued Nov. 15, 1977.

I claim:

1. A prostaglandin analog of the formula

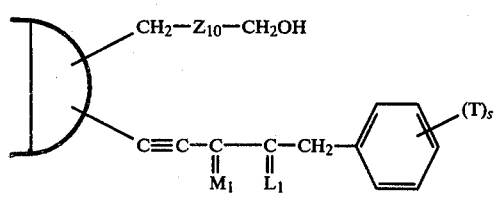

wherein D is

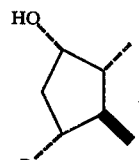

or

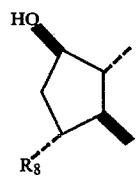

wherein $R_8$ is hydrogen or hydroxy;
wherein $M_1$ is

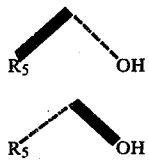

or wherein $R_5$ is hydrogen or methyl;
wherein $L_1$ is

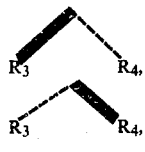

or a mixture of

and

-continued wherein $R_3$ and $R_4$ are hydrogen or methyl being the same or different;
wherein $Z_{10}$ is
(1) cis—CH=CH—CH—$(CH_2)_g$—$CH_2$—,
(2) cis—CH=CH—$CH_2$—$(CH_2)_g$—$CF_2$—,
(3) cis—$CH_2$—CH=CH—$(CH_2)_g$—$CH_2$—,
(4) —$(CH_2)_3$—$(CH_2)_g$—$CH_2$,
(5) —$(CH_2)_3$—$(CH_2)_g$—$CF_2$—, or
(6) —$CH_2$—O—$CH_2$—$(CH_2)_g$—$CH_2$—,
wherein g is one, 2, or 3; and
wherein s is one to 3, inclusive and T is chloro, fluoro, trifluoromethyl, alkyl of one to 3 carbon atoms, inclusive, or alkoxy of one to 3 carbon atoms, inclusive, the various T's being the same or different, with the proviso that not more than two are other than alkyl.

2. A prostaglandin analog according to claim 1, wherein D is

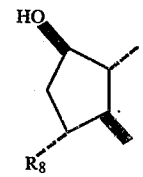

3. A prostaglandin analog according to claim 2, wherein $R_8$ is hydrogen.

4. A prostaglandin analog according to claim 2, wherein $R_8$ is hydroxy.

5. A prostaglandin analog according to claim 1, wherein D is

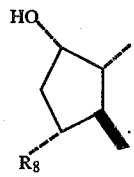

6. A prostaglandin analog according to claim 5, wherein $Z_{10}$ is cis—CH=CH—$CH_2$—$(CH_2)_g$—$CF_2$—.

7. 2-Decarboxy-2-hydroxymethyl-2,2-difluoro-13,14-didehydro-17-phenyl-17,18,19,20-tetranor-PGF$_{2\alpha}$, a prostaglandin analog according to claim 6.

8. A prostaglandin analog according to claim 5, wherein $Z_{10}$ is —$(CH_2)_3$—$(CH_2)_g$—$CF_2$—.

9. 2-Decarboxy-2-hydroxymethyl-2,2-difluoro-13,14-didehydro-17-phenyl-17,18,19,20-tetranor-PGF$_{1\alpha}$, a prostaglandin analog according to claim 8.

10. A prostaglandin analog according to claim 5, wherein $Z_{10}$ is cis—$CH_2CH$=CH—$(CH_{2l})_g$—$CH_2$—.

11. 2-Decarboxy-2-hydroxymethyl-cis-4,5-didehydro-13,14-didehydro-17-phenyl-17,18,19,20-tetranor-PGF$_{1\alpha}$, a prostaglandin analog according to claim 10.

12. A prostaglandin analog according to claim 5, wherein $Z_{10}$ is —$CH_2$—O—$CH_2$—$(CH_2)_g$—$CH_2$—.

13. 2-Decarboxy-2-hydroxymethyl-5-oxa-13,14-didehydro-17-phenyl-17,18,19,20-tetranor-PGF$_{1\alpha}$, a prostaglandin analog according to claim 12.

14. A prostaglandin analog according to claim 5, wherein $Z_{10}$ is —$(CH_2)_3$—$(CH_2)_g$—$CH_2$—.

15. A prostaglandin analog according to claim 14, wherein $M_1$ is

16. 2-Decarboxy-2-hydroxymethyl-15-epi-13,14-didehydro-17-phenyl-17,18,19,20-tetranor-PGF$_{1\alpha}$, a prostaglandin analog according to claim 15.

17. A prostaglandin analog according to claim 14, wherein $M_1$ is

18. A prostaglandin analog according to claim 17, wherein m is 3.

19. A prostaglandin analog according to claim 18, wherein g is 3.

20. 2-Decarboxy-2-hydroxymethyl-2a,2b-dihomo-15-methyl-13,14-didehydro-17-phenyl-17,18,19,20-tetranor-PGF$_{1\alpha}$, a prostaglandin analog according to claim 19.

21. 2-Decarboxy-2-hydroxymethyl-2a,2b-dihomo-13,14-didehydro-17-phenyl-17,18,19,20-tetranor-PGF$_{1\alpha}$, a prostaglandin analog according to claim 19.

22. A prostaglandin analog according to claim 18, wherein g is 1.

23. A prostaglandin analog according to claim 22, wherein at least one of $R_3$ and $R_4$ is methyl.

24. A prostaglandin analog according to claim 23, wherein $R_3$ and $R_4$ are both methyl.

25. 2-Decarboxy-2-hydroxymethyl-13,14-didehydro-16,16-dimethyl-17-phenyl-18,19,20-trinor-PGF$_{1\alpha}$, a prostaglandin analog according to claim 24.

26. A prostaglandin analog according to claim 22, wherein at least two of $R_3$, $R_4$, and $R_5$ are methyl.

27. A prostaglandin analog according to claim 26, wherein $R_3$, $R_4$, and $R_5$ are all methyl.

28. 2-Decarboxy-2-hydroxymethyl-15,16,16-trimethyl-13,14-didehydro-17-phenyl-18,19,20-trinor-PGF$_{1\alpha}$, a prostaglandin analog according to claim 27.

29. A prostaglandin analog according to claim 22, wherein $R_3$ and $R_4$ are both hydrogen.

30. A prostaglandin analog according to claim 29, wherein $R_5$ is methyl.

31. 2-Decarboxy-2-hydroxymethyl-15-methyl-13,14-didehydro-17-phenyl-17,18,19,20-tetranor-PGF$_{1\alpha}$, a prostaglandin analog according to claim 30.

32. A prostaglandin analog according to claim 29, wherein $R_5$ is hydrogen.

33. 2-Decarboxy-2-hydroxymethyl-13,14-didehydro-17-phenyl-17,18,19,20-tetranor-PGF$_{1\alpha}$, a prostaglandin analog according to claim 32.

34. A prostaglandin analog according to claim 5, wherein $Z_{10}$ is cis—$CH=CH$—$CH_2$—$(CH_2)_g$—$CH_2$—.

35. A prostaglandin analog according to claim 34, wherein $M_1$ is

36. A prostaglandin analog according to claim 35, wherein m is 3.

37. A prostaglandin analog according to claim 36, wherein g is 3.

38. 2-Decarboxy-2-hydroxymethyl-2a,2b-dihomo-15-epi-13,14-didehydro-17-phenyl-17,18,19,20-tetranor-PGF$_{2\alpha}$, a prostaglandin analog according to claim 37.

39. A prostaglandin analog according to claim 36, wherein g is 1.

40. A prostaglandin analog according to claim 39, wherein at least one of $R_3$ and $R_4$ is methyl.

41. 2-Decarboxy-2-hydroxymethyl-15-epi-13,14-didehydro-16-methyl-17-phenyl-18,19,20-trinor-PGF$_{2\alpha}$, a prostaglandin analog according to claim 40.

42. A prostaglandin analog according to claim 39, wherein at least two of $R_3$, $R_4$, and $R_5$ are methyl.

43. 2-Decarboxy-2-hydroxymethyl-15-epi-15,16-dimethyl-13,14-didehydro-17-phenyl-18,19,20-trinor-PGF$_{2\alpha}$, a prostaglandin analog according to claim 42.

44. A prostaglandin analog according to claim 39, wherein $R_3$ and $R_4$ are both hydrogen.

45. 2-Decarboxy-2-hydroxymethyl-15-epi-15-methyl-13,14-didehydro-17-phenyl-17,18,19,20-tetranor-PGE$_{2\alpha}$, a prostaglandin analog according to claim 44.

46. A prostaglandin analog according to claim 34, wherein $M_1$ is

47. A prostaglandin analog according to claim 46, wherein m is 3.

48. A prostaglandin analog according to claim 47, wherein g is 3.

49. A prostaglandin analog according to claim 48, wherein at least one of $R_3$ and $R_4$ is methyl.

50. 2-Decarboxy-2-hydroxymethyl-2a,2b-dihomo-16,16-dimethyl-13,14-didehydro-17-phenyl-17,18,19,20-tetranor-PGF$_{2\alpha}$, a prostaglandin analog according to claim 49.

51. A prostaglandin analog according to claim 48, wherein at least two of $R_3$, $R_4$, and $R_5$ are methyl.

52. 2-Decarboxy-2-hydroxymethyl-2a,2b-dihomo-15,16-dimethyl-13,14-didehydro-17-phenyl-18,19,20-trinor-PGF$_{2\alpha}$, a prostaglandin analog according to claim 51.

53. A prostaglandin analog according to claim 48, wherein $R_3$ and $R_4$ are both hydrogen.

54. 2-Decarboxy-2-hydroxymethyl-2a,2b-dihomo-15-methyl-13,14-didehydro-17-phenyl-17,18,19,20-tetranor-PGF$_{2\alpha}$, a prostaglandin analog according to claim 53.

55. A prostaglandin analog according to claim 47, wherein g is 1.

56. A prostaglandin analog according to claim 55, wherein at least one of $R_3$ and $R_4$ is methyl.

57. A prostaglandin analog according to claim 56, wherein only one of $R_3$ and $R_4$ is methyl.

58. 2-Decarboxy-2-hydroxymethyl-13,14-didehydro-16-methyl-17-phenyl-18,19,20-trinor-PGF$_{2\alpha}$, a prostaglandin analog according to claim 57.

59. A prostaglandin analog according to claim 56, wherein $R_3$ and $R_4$ are both methyl.

60. 2-Decarboxy-2-hydroxymethyl-13,14-didehydro-16,16-dimethyl-17-phenyl-18,19,20-trinor-PGF$_{2\alpha}$, a prostaglandin analog according to claim 59.

61. A prostaglandin analog according to claim 55, wherein at least one of $R_3$ and $R_4$ is fluoro.

62. A prostaglandin analog according to claim 61, wherein $R_2$ and $R_4$ are both fluoro.

63. A prostaglandin analog according to claim 62, wherein $R_5$ is methyl.

64. 2-Decarboxy-2-hydroxymethyl-15-methyl-16,16-difluoro-13,14-didehydro-17-phenyl-17,18,19,20-tetranor-PGF$_2\alpha$, a prostaglandin analog according to claim 63.

65. A prostaglandin analog according to claim 62, wherein $R_5$ is hydrogen.

66. 2-Decarboxy-2-hydroxymethyl-16,16-difluoro-13,14-didehydro-17-phenyl-17,18,19,20-tetranor-PGF$_2\alpha$, a prostaglandin analog according to claim 65.

67. A prostaglandin analog according to claim 55, wherein $R_3$ and $R_4$ are both hydrogen.

68. A prostaglandin analog according to claim 67, wherein $R_5$ is methyl.

69. 2-Decarboxy-2-hydroxymethyl-15-methyl-13,14-didehydro-17-phenyl-17,18,19,20-tetranor-PGF$_2\alpha$, a prostaglandin analog according to claim 68.

70. A prostaglandin analog according to claim 67, wherein $R_5$ is hydrogen.

71. 2-Decarboxy-2-hydroxymethyl-13,14-didehydro-17-phenyl-17,18,19,20-tetranor-PGF$_2\alpha$, a prostaglandin analog according to claim 70.

* * * * *

UNITED STATES PATENT OFFICE
CERTIFICATE OF CORRECTION

Patent No. 4,206,311                    Dated   3 June 1980

Inventor(s)   Herman W. Smith

It is certified that error appears in the above-identified patent and that said Letters Patent are hereby corrected as shown below:

Column 2, lines 6-7, "$R_3$ and $R_4$ are hydrogen or methyl being the same or different" should read -- $R_3$ and $R_4$ are hydrogen, methyl, or fluoro, being the same or different, with the proviso that one of $R_3$ and $R_4$ is methyl only when the other is hydrogen; --; line 9, "cis-CH=CH-CH-$(CH_2)_g$-$CH_2$-," should read -- cis-CH=CH-$CH_2$-$(CH_2)_g$-$CH_2$-, --; line 16, wherein s is one to 3," should read -- wherein s is zero to 3, --; line 52, 57, 61, 62, and 67, "17,18,19,20-tetranor-" should read -- 18,19,20-trinor- --;

Column 3, line 10, 24-25, 28, 51, and 56, "17,18,19,20-tetranor-" should read -- 18,19,20-trinor- --; lines 19-20 and 23-25 delete claims 18 and 20; line 21, "according to claim 18" should read -- according to claim 17 --;

Column 4, line 1, "according to claim 36" should read -- according to claim 35 --; line 4, 21, 38, and 50-51, "17,18,19,20-tetranor-" should read -- 18,19,20-trinor- --; lines 30-31, delete claim 47; line 32, "according to claim 47" should read -- according to claim 46 --; line 22, "$PGE_2\alpha$" should read -- $PGF_2\alpha$ --;

Column 5, line 2, "$R_2$ and $R_4$" should read -- $R_3$ and $R_4$ --; lines 6-7 and line 12, "17,18,19,20-tetranor-" should read -- 18,19,20-trinor- --;

Column 6, line 6 and line 11, "17,18,19,20-tetranor-" should read -- 18,19,20-trinor- --.

Signed and Sealed this

Twenty-third Day of September 1980

[SEAL]

Attest:

SIDNEY A. DIAMOND

Attesting Officer                    Commissioner of Patents and Trademarks